United States Patent [19]

Tautvydas et al.

[11] Patent Number: 5,407,445
[45] Date of Patent: Apr. 18, 1995

[54] GEL COMPOSITION FOR IMPLANT PROSTHESIS AND METHOD OF USE

[75] Inventors: Daiva K. Tautvydas, Atlanta; Mannarsamy Balasubramanian, Roswell; R. Martin Emanuele, Alpharetta, all of Ga.

[73] Assignee: Cytrx Corporation, Norcross, Ga.

[21] Appl. No.: 64,519

[22] Filed: May 19, 1993

Related U.S. Application Data

[63] Continuation-in-part of Ser. No. 886,264, May 20, 1992, abandoned.

[51] Int. Cl.⁶ .................................................. A61F 2/12
[52] U.S. Cl. .................................... 623/8; 623/11; 623/66
[58] Field of Search ............... 623/11, 16, 66; 528/76; 424/422

[56] References Cited

U.S. PATENT DOCUMENTS

| | | |
|---|---|---|
| 3,293,663 | 12/1966 | Cronin . |
| 3,665,520 | 5/1972 | Perras et al. . |
| 3,681,787 | 8/1972 | Perras . |
| 3,683,424 | 8/1972 | Pangman . |
| 3,919,724 | 11/1975 | Sanders et al. . |
| 4,095,295 | 6/1978 | Lake . |
| 4,143,428 | 3/1979 | Cohen . |
| 4,298,997 | 11/1981 | Rybka . |
| 4,298,998 | 11/1981 | Naficy . |
| 4,433,440 | 2/1984 | Cohen . |
| 4,507,810 | 4/1985 | Bartholdson . |
| 4,573,999 | 3/1986 | Netto . |
| 4,610,690 | 9/1986 | Tiffany . |
| 4,636,213 | 1/1987 | Pakian . |
| 4,648,880 | 3/1987 | Brauman . |
| 4,650,487 | 3/1987 | Chaglassian . |
| 4,657,553 | 4/1987 | Taylor . |
| 4,702,917 | 10/1987 | Schindler . |
| 4,713,073 | 12/1987 | Reinmuller . |
| 4,731,081 | 3/1988 | Tiffany et al. . |
| 4,740,208 | 4/1988 | Cavon . |
| 4,769,036 | 9/1988 | Moder . |
| 4,772,284 | 9/1988 | Jefferies et al. . |
| 4,772,285 | 9/1988 | Ksander et al. . |
| 4,773,909 | 9/1988 | Chaglassian . |
| 4,790,848 | 12/1988 | Cronin . |
| 4,795,463 | 1/1989 | Gerow . |
| 4,820,302 | 4/1989 | Woodroof . |
| 4,820,303 | 4/1989 | Brauman . |
| 4,822,741 | 4/1989 | Bares . |
| 4,828,561 | 5/1989 | Woodroff . |
| 4,839,280 | 6/1989 | Bares . |
| 4,840,628 | 6/1989 | Cavon . |
| 4,902,511 | 2/1990 | Kronman . |
| 4,912,141 | 3/1990 | Kronman . |
| 4,936,858 | 6/1990 | O'Keeffe . |
| 4,955,909 | 9/1990 | Ersek et al. . |
| 4,963,150 | 10/1990 | Brauman . |
| 4,995,882 | 2/1991 | Destouet et al. . |
| 5,019,100 | 5/1991 | Hennink et al. . |
| 5,067,965 | 11/1991 | Ersek et al. . |
| 5,120,816 | 6/1992 | Gould et al. . |

OTHER PUBLICATIONS

Touchette, N., "Research In Focus–Silicone Implants and Autoimmune Disease: Studies Fail to Gel," *The Journal of NIH Research*, vol. 4, pp.49–52 (May 1992).

Gladwell, M., "FDA Will Allow Limited Use of Silicone–Gel Breast Implants", *the Washington Post*, Section A, Final Edition, p. 902 (Apr. 17, 1992).

Goin, J., "High–Pressure Injection of Silicone Gel Into An Axilla–A Complication of Closed Compression Capsulotomy Of The Breast," *Plastic & Reconstructive Surgery*, vol. 62, No. 6, pp. 891–895 (Dec, 1978).

Spancake, C. et al., "Thermorheologic Properties of Aqueous Sol and Gels of Tetronic 1508," *Pharmaceutical Research*, vol. 8, No. 3, pp. 345–349 (1991).

Lenaerts, V., "Temperature-dependent rheological behaviour of Pluronic F-126 aqueous solutions", *Int. Journal of Pharm.*, vol. 39, pp. 121–127 (1987).

*Primary Examiner*—David Isabella
*Attorney, Agent, or Firm*—Jones & Askew

[57] ABSTRACT

In accordance with the present invention, a composition and method is provided for a biocompatible filler for prostheses. The composition and method relate to certain polyoxyethylene/polyoxypropylene block co-polymers which have gelling properties at body temperature and are ideally suited for use as fillers for a soft tissue prosthesis such as a breast implant.

16 Claims, 10 Drawing Sheets

Typical Test Curve (Sample 14 at 37C)

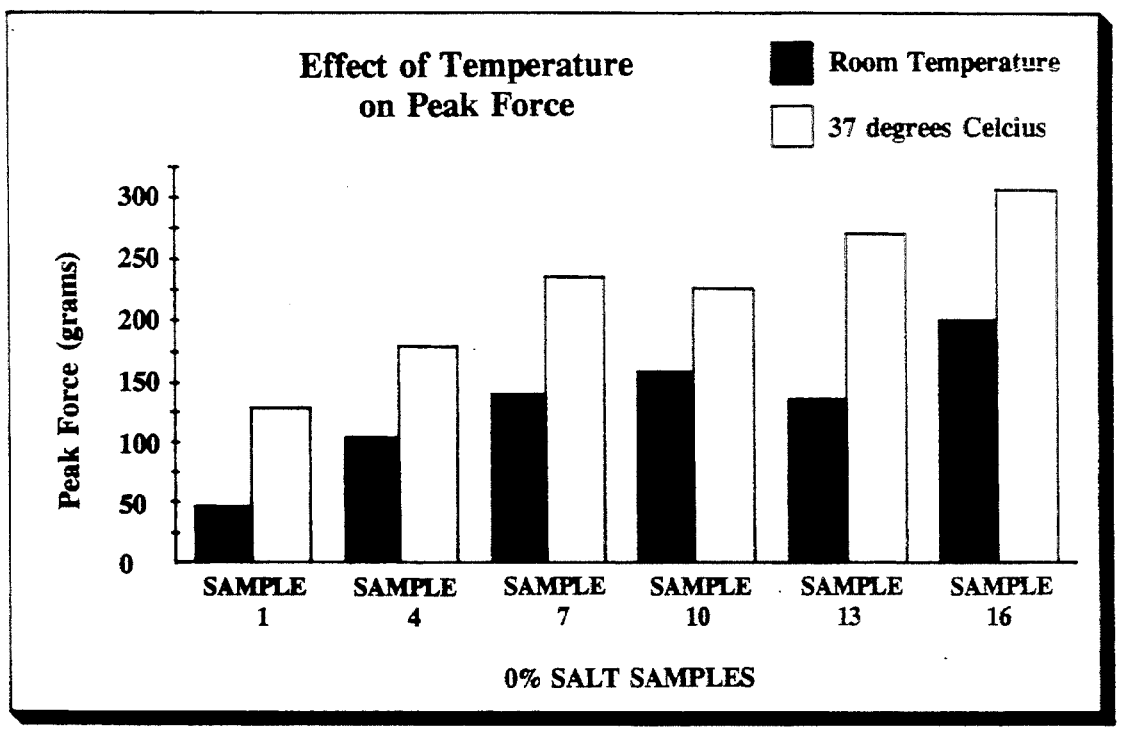
Fig_10
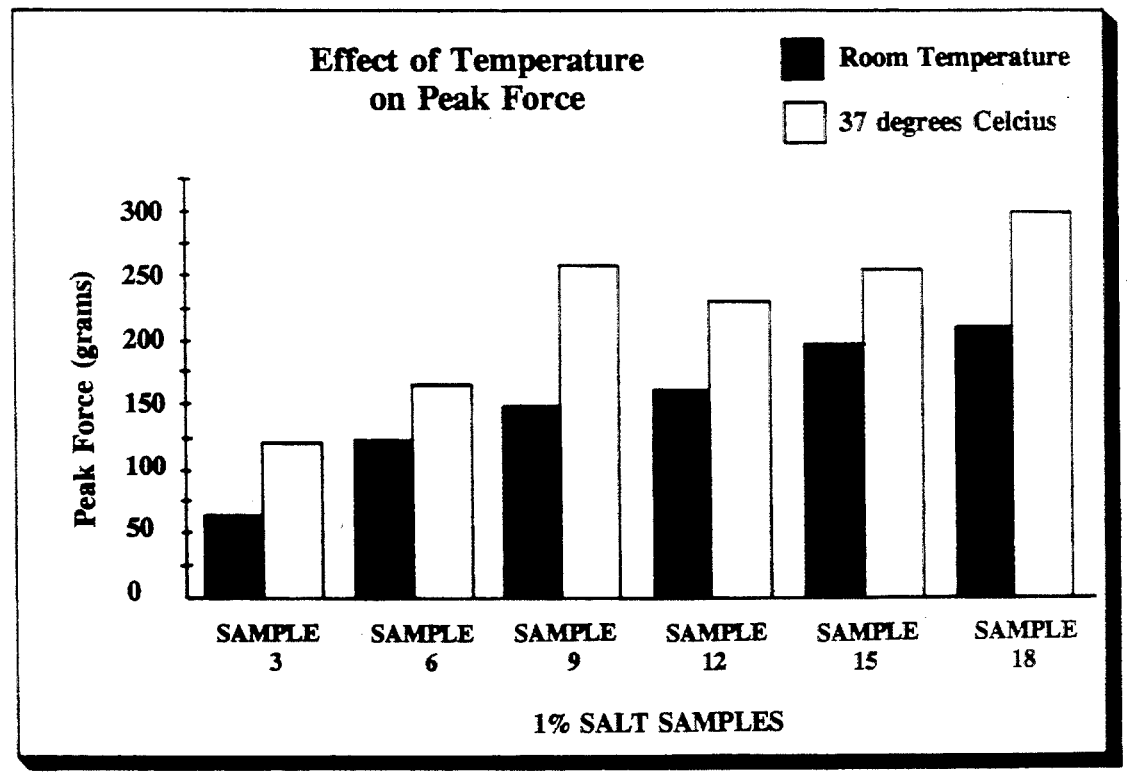
Fig_11

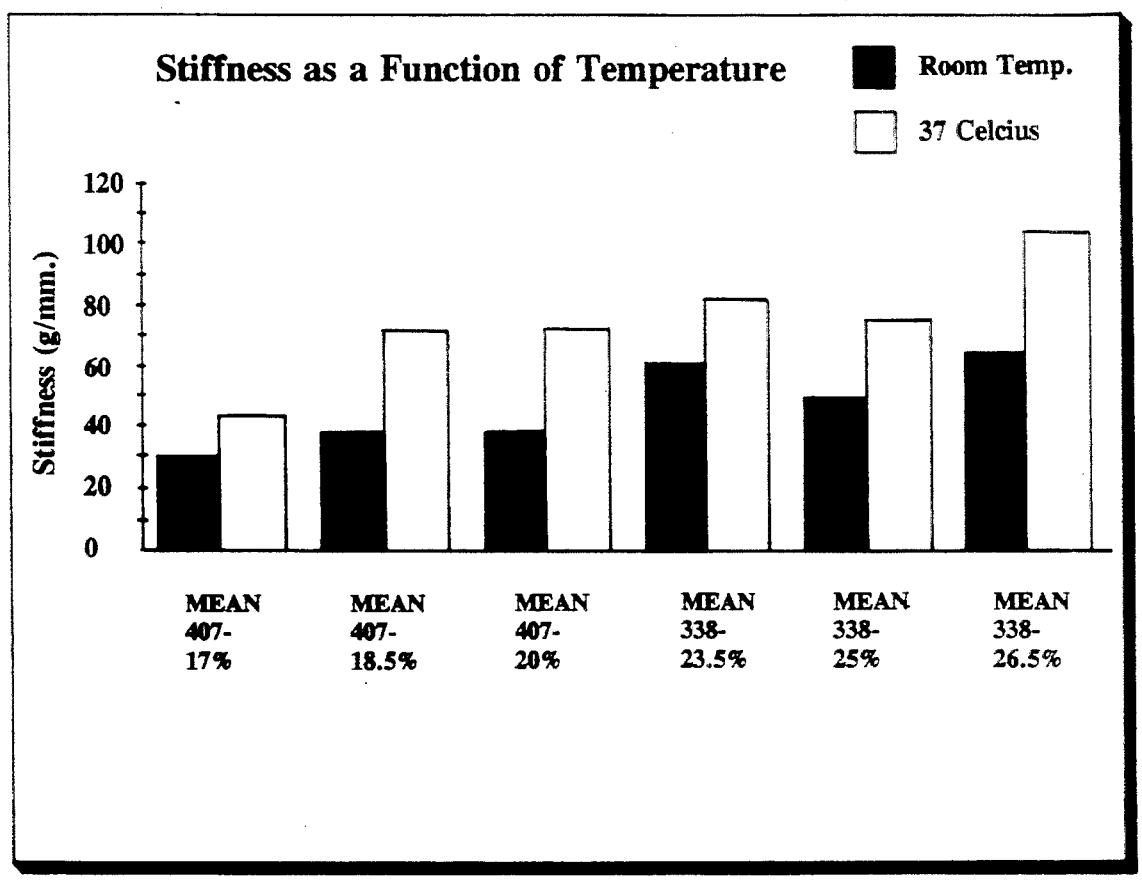
Fig_12

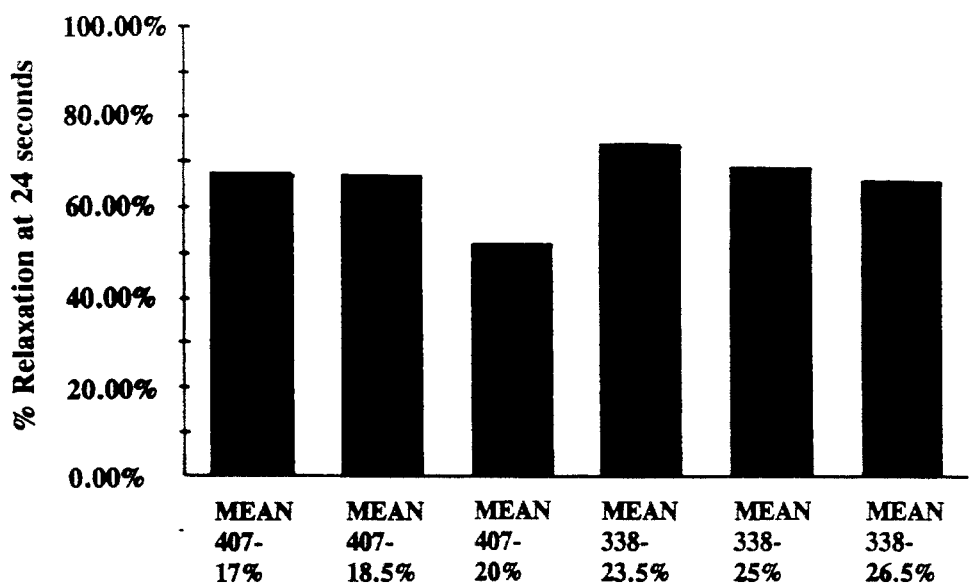
Fig_13
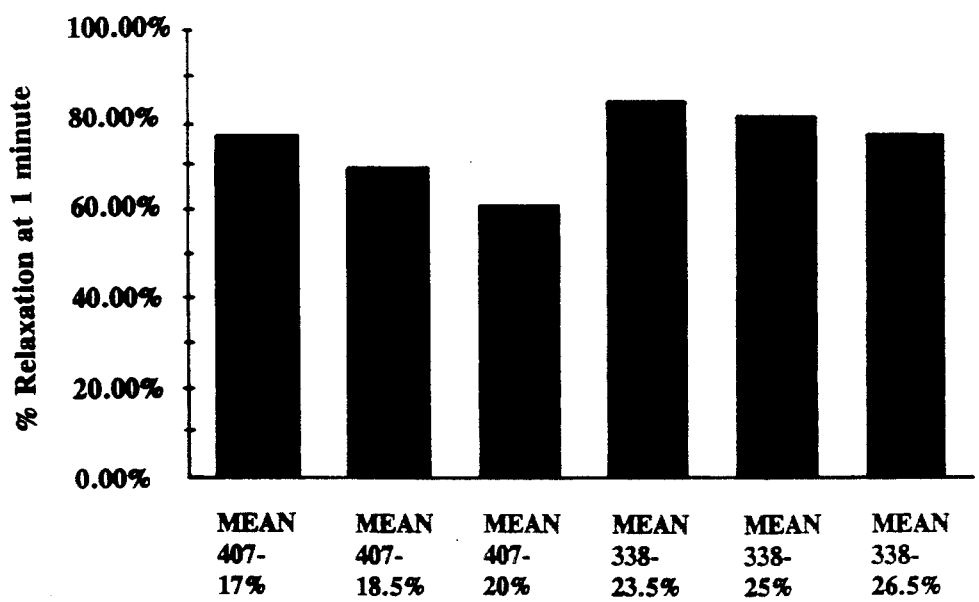
Fig_14

GEL COMPOSITION FOR IMPLANT PROSTHESIS AND METHOD OF USE

CROSS-REFERENCE TO RELATED APPLICATIONS

This is a continuation-in-part patent application of U.S. patent application Ser. No. 07/886,264, filed on May 20, 1992, now abandoned.

TECHNICAL FIELD

The present invention relates to a biocompatible gel composition for use in implantable prostheses. More particularly, the present invention relates to certain polyoxyethylene/polyoxypropylene block copolymers which have gelling properties that make them ideally suited for use as fillers for a soft tissue prosthesis such as a breast implant.

BACKGROUND OF THE INVENTION

As used herein, the term "prosthesis" means any device that is implanted into the body of a human or animal to replace or supplement a body part. The term "soft tissue" refers to pliable, soft biological tissues such as muscle, fat and skin.

Implantable prostheses for correcting contour defects and form limitations in the human body have been in use since at least the early 1950's. The procedure has been frequently used for breast reconstruction, either following traumatic injury or surgical loss of the breast tissue, as through radical mastectomy, or to correct developmental hypoplasia. The procedure has also been used for cosmetic breast augmentation. Although the composition of the present invention can be used for reconstruction of any soft tissues, the discussion which follows is directed to reconstruction and augmentation of the breast tissue.

Early implants typically consisted of a foam or sponge material. These implants had two critical disadvantages. First, body tissue eventually invaded the sponge material, forming a hard scar which was painful and affected the consistency of the breast. The second disadvantage was that the sponge implant itself did not have the feel of a natural breast.

Later, breast prostheses were introduced comprising flexible sacs or lumens containing some type of soft gel filling. For example, an early breast prosthesis having this structure is described in U.S. Pat. No. 3,293,663 to Conin. The device disclosed in U.S. Pat. No. 3,293,663 comprises a silicone rubber molded flexible cup having a flat back and containing silicone gel. Silicone gel was used because it approximated the consistency of breast tissue and was thought, at the time, to be relatively non-toxic.

The combination of a lumen containing a substance approximating the consistency of breast tissue is still being used today. The lumen or sac is generally comprised of silicone rubber, Teflon, dacron, polyurethane or other plastic prosthesis materials. Typically such an implant has consisted of a flexible outer shell member made from silicone rubber, polyurethane or other known durable biocompatible polymer which has an elastic memory, and which is configured to a shape dedicated to provide the desired bodily contour. The generally hollow shell member or lumen may consist of a single layer or numerous layers in which one shell is placed inside the other. A variety of structural changes have been made to the early implants in an attempt to approximate the consistency and appearance of the human breast and to avoid the negative biological affects associated with introducing a foreign structure into the body.

For example, U.S. Pat. No. 4,573,999 to Netto describes a prosthetic implant for human breasts wherein the exterior surface of the lumen has concentric waves which serve to relieve the pressure caused by capsular contracture without reducing the volume or firmness of the implant. U.S. Pat. No. 4,790,848 describes a multiple lumen breast prosthesis in which the innermost lumen is spherical and free-floating to better approximate the natural movement of breast tissue. U.S. Pat. No. 4,650,487 to Chaylassian describes a multilumen breast lo prosthesis in which the lumens are filled with various substances to allow adjustment of the volume of the prosthesis.

The various lumens currently used are subject to a variety of mechanical breakdowns. For example, shell breakdown and rupture often occurs when the filler is a poor lubricant. This type of bag wall failure is known as "fold flaw." Several theories have been advanced to explain why the lumen ruptures. Fold flaw has been attributed to the stress differential between the inner and outer surfaces of a bag wall section and a creased area caused by one wall surface being in compression and the other being in tension. Fold flaw has also been attributed to friction between the opposing walls and changes in the physical properties of the lumen over a prolonged period of maintaining a crease. In any case, mechanical failure of the lumen results in introduction of the interior substances into the body cavity.

Shell rupture and breakdown can also occur by exterior mechanical manipulation of the breast. Such manipulation is sometimes necessary to rupture the capsule which naturally forms around the implant when an organism attempts to protect itself against invasion be a foreign body. Typically, an implant will be rapidly encapsulated by a fibrous structure composed primarily of collagen and glycosaminoglycans and containing fibroblasts and histiocytes. The capsule then contracts, resulting in hardening and spherical deformation of the implant and the surrounding tissue. This process is known as capsular contracture. The capsule becomes painful and deformed in appearance and usually must be ruptured or broken when it develops. The mechanical process of rupturing the capsule can cause the implant itself to rupture and its contents to leak into the body cavity.

Various attempts have been made to avoid the development of capsular contracture. For example, U.S. Pat. No. 4,772,285 describes a collagen coated soft tissue prosthesis for that purpose. However, these methods have been unsuccessful and the risk of leaks and ruptures remains high. Thus, it is critical that the adverse biological effects of the filler material be minimal.

U.S. Pat. Nos. 4,740,208 and 4,840,628 to Cavon describe cast, uncontained, silicone gel elastomer implantable prostheses. U.S. Pat. No. 4,657,553 describes a soft tissue implant composed of a hydrogel filler comprising a gellable polysaccharide and/or a protein or polypeptide, and a polymer of a hydrophilic acrylic and/or methacrylic acid derivative. U.S. Pat. No. 4,772,284 to Jefferies et al. describes a biocompatible material suitable for implant use which comprises a purified reconstituted collagen gel and a purified gel of alpha-amino acid homopolymers or random copolymers. U.S. Pat.

No. 5,067,965 to Ersek et al. discloses a bio-osmotic gel for filling implant lumens with improved radiolucence consisting of a bioosmotic gel containing polyvinylpyrolidone and a biocompatible salt.

Many different substances have been used to fill the lumen of the implant. Examples of these include normal saline, foam pads, and silicone oil or silicone gel. Each of these prior materials, however, exhibit at least one major drawback. Saline, for example, is a poor lubricating agent and prostheses filled only with saline have been known to undergo accelerated shell breakdown and rupture due to friction of the inner shell rubbing against itself (fold flaw). Molded foam inserts were found to rapidly calcify after implantation in the body and do not feel or look like natural breast tissue.

After a considerable period of time, silicone oil remains the most commonly used filling material. With respect to most implant prostheses, including breast implants, the filler is normally utilized in the form of a partially vulcanized silicone which is sealed inside the lumen prior to implant. This material has enjoyed a long period of use principally because of two desirable properties. Silicone oil is a natural lubricant and this tends to prevent shell breakdowns occasioned by internal friction. In addition, the viscosity of silicone oil placed inside a partially inflated lumen imparts a consistency to the structure which closely predicates natural breast tissue.

Recently, the use of silicone in prostheses has been severely limited in the United States by the Food and Drug Administration due to the lack of safety data regarding its use and an increase in awareness of adverse biological effects caused by leakage of silicone into the body cavity. The use of silicone oil and gel presents several major disadvantages. One such disadvantage involves the inability of the body to eliminate silicone oil. The silicone oil continually migrates or leaches through the wall of the implant into surrounding tissue where it is not eliminated from the body. The silicone oil can accumulate and produce a painful inflammatory reaction. Silicone oil may also be associated with the formation of autoimmune disease. N. Touchette, "Silicone Implants and Autoimmune Disease: Studies Fail to Gel", J. NIH RESEARCH, Vol. 4, pp. 49-52 (May 1992). In the case of traumatic rupture of the shell, silicone is forced into the surrounding tissues, traveling down the facial planes where it causes a severe foreign body reaction and requires extensive surgery to remove. An additional drawback with respect to silicone oil is that it is radiographically dense. This makes it more difficult to examine the area of implant by X-ray, or the like. This may obscure mammogram detail and delay detection of breast cancer.

Thus, what is needed is a composition for filling the lumen of a prosthesis that has the consistency and feel of natural tissue and, that is non-toxic so that if the prosthesis should leak or burst, the composition will not cause any adverse biological effects. What is further needed is a composition for filling the lumen of a prosthesis that is radioluscent so that it does not interfere with x-ray detection of abnormalities in tissues surrounding the prosthesis. The composition should also serve to lubricate the interior of the prosthesis to avoid mechanical breakdown of the shell of the prosthesis. What is further needed is a composition that would be resistant to the formation of a fibrous capsule leading to contracture and possible rupture.

SUMMARY OF THE INVENTION

In accordance with the present invention, a unique gel filler system for implant lumens is provided which eliminates the drawbacks discussed above. The gel of the present invention is a biocompatible polymeric material, preferably in an aqueous solution, which is stable to sterilization. The polymeric materials which encompass the present invention are polyoxyethylene/polyoxypropylene block copolymers.

The preferred composition according to the present invention comprises a solution of polyoxyethylene-polyoxypropylene block copolymer with the following general formula:

$$HO(C_2H_4O)_b(C_3H_6O)_a(C_2H_4O)_bH$$

wherein a is an integer such that the hydrophobe represented by $(C_3H_6O)_a$ has a molecular weight of at least 1750 Daltons and b is an integer such that the hydrophile portion represented by $(C_2H_4O)_b$ constitutes from about 10 to 90 percent by weight of the copolymer, with the preferable range of hydrophile portion being between 50% and 90%.

The preparation of aqueous gels of polyoxyethylene-polyoxypropylene block copolymers is described in U.S. Pat. Nos. 3,867,533: 3,748,276; and 3,740,421, all of which are incorporated herein by reference. None of the aforementioned patents disclose using these copolymers in a prosthesis such as a breast implant.

Because certain of these polyoxyethylene-polyoxypropylene block copolymers are liquids at low temperatures, and gels at body temperatures, the aqueous gel compositions are ideal for filling a prosthesis such as a breast implant. This family of polyoxyethylene-polyoxypropylene block copolymers is also substantially non-toxic, and exhibits improved lubrication and improved radiolucence. The copolymers are also biocompatible. If the implant should leak or burst and the copolymer be released into the body, the copolymer is quickly eliminated from the body without causing any adverse biological effects.

Accordingly, it is an object of the present invention to provide a safe and effective composition and method for filling the lumen of a prosthesis.

It is another object of the present invention to provide a composition and method for filling the lumen of a prosthesis to provide a safe and effective breast implant prosthesis.

It is yet another object of the present invention to provide a composition for filling the lumen of a prosthesis that is biocompatible and will not cause adverse biological effects if the prosthesis should leak or burst.

It is another object of the present invention to provide a composition for filling the lumen of a prosthesis which is similar in consistency and feel to the natural human breast.

Yet another object of the present invention is to provide a composition for filling the lumen of a prosthesis which has improved lubricating properties so as to decrease the occurrence of fold flaw ruptures and leaks of the prosthesis resulting from stress caused to the lumen of the prosthesis in the course of natural movement.

Another object of the present invention is to provide a composition for filling the lumen of a soft tissue prosthesis which has improved radiolucency.

Another object of the present invention is to provide a composition of the outer shell membrane which incorporates covalently linked glycosaminoglycans thereby inhibiting or preventing the formation of fibrous capsule prone to contracture.

These and other objects, features and advantages of the present invention will become apparent after a review of the following detailed description of the disclosed embodiments and the appended claims.

BRIEF DESCRIPTION OF THE DRAWINGS

FIG. 10 shows temperature effect of 0% salt concentration on peak force.

FIG. 11 shows temperature effect of 1% salt concentration on peak force.

FIG. 12 shows stiffness of the gels as a function of temperature.

FIG. 13 shows percent relaxation at 24 seconds of the gels as a function of concentration of the gel.

FIG. 14 shows percent relaxation at 1 minute of the gels as a function of concentration of the gel.

DETAILED DESCRIPTION OF THE DISCLOSED EMBODIMENTS

Figure 1:
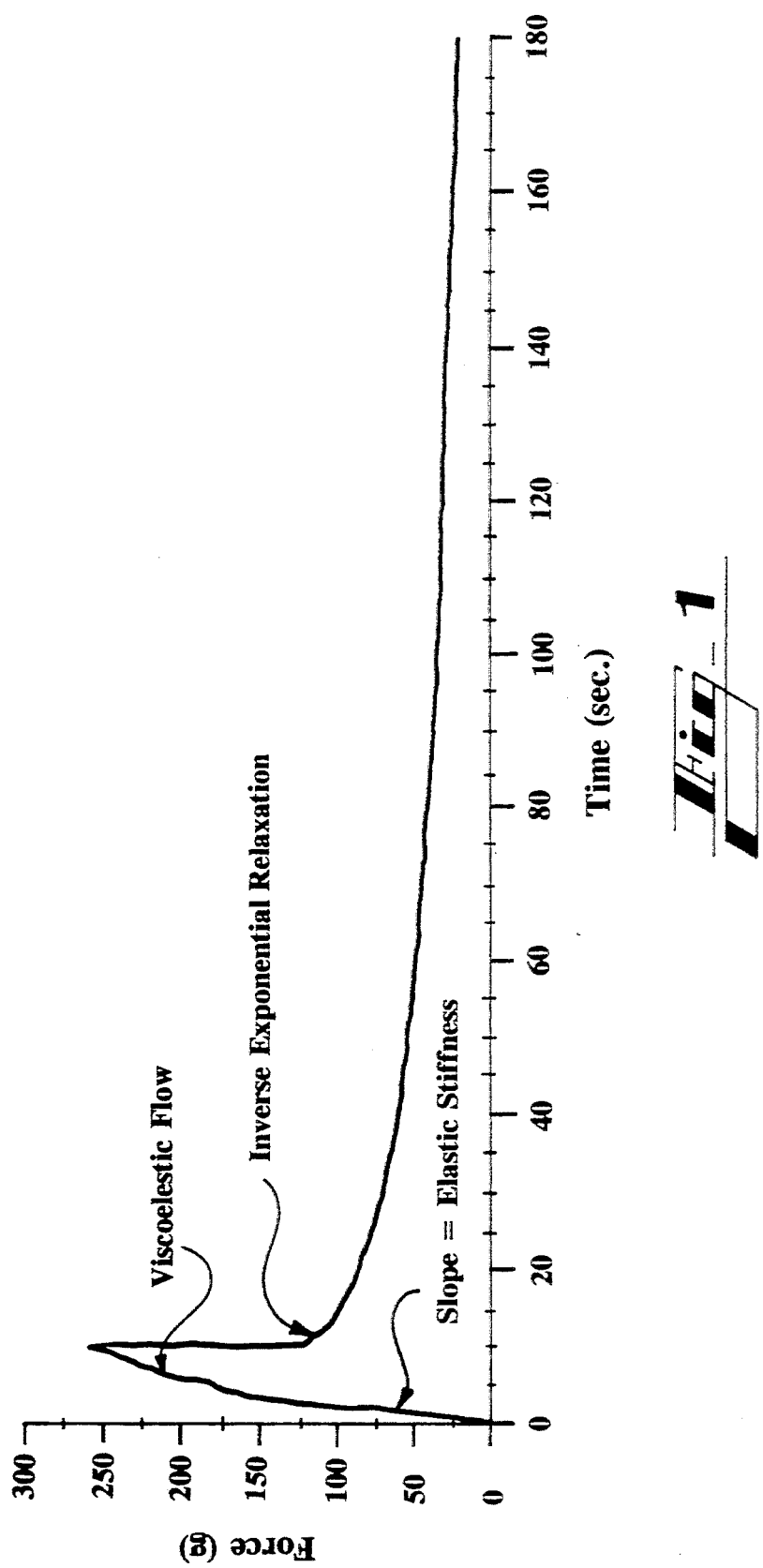
FIG. 1 is a typical test curve showing percent relaxation over time.

The present invention contemplates a biocompatible gel comprising a solution of a polyoxyethylene/polyoxypropylene block copolymer. These biocompatible gels are particularly suited for filling the lumen of a soft tissue prosthesis that can be used in a human or animal. The present invention is particularly useful for filling breast implant devices.

The aqueous gel composition of the present invention comprises a solution of a polyoxyethylene-polyoxypropylene block copolymer that has the physical property of being a liquid at room temperature or below and a gel at body temperature.

The polyoxyethylene-polyoxypropylene block copolymer has the following general formula:

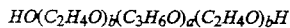

wherein a is an integer such that the hydrophobe represented by $(C_3H_6O)_a$ has a molecular weight of at least 1750 Daltons and b is an integer such that the hydrophile portion represented by $(C_2H_4O)_b$ constitutes from about 50 to 90 percent by weight of the copolymer.

The polyoxyethylene-polyoxypropylene block copolymer preferably has a hydrophobe represented by $(C_3H_6O)_a$ with a molecular weight between approximately 1750 and 6000 Daltons with the most preferable molecular weight of the $(C_3H_6O)_b$ between 3000 and 4000 Daltons. It is to be understood that the polyoxyethylene-polyoxypropylene block copolymer of the present invention can be chemically bonded or cross-linked depending upon the gelling properties desired.

The surface active copolymer blocks are formed by condensation of propylene oxide and ethylene oxide at elevated temperature and pressure in the presence of a basic catalyst. There is some statistical variation in the number of monomer units which combine to form a polymer chain in each copolymer. The molecular weights given are approximations of the average weight of copolymer molecule in each preparation. It is to be understood that the blocks of propylene oxide and ethylene oxide do not have to be pure. Small amounts of other materials can be admixed so long as the overall physical chemical properties are not substantially changed. A more detailed discussion of the preparation of these products is found in U.S. Pat. No. 2,674,619, which is incorporated herein by reference.

Preparation of the copolymer portion of the present invention is described in U.S. Pat. Nos. 3,925,241 and 3,867,533, both of which are incorporated herein by reference. Illustrative block copolymers of the following general formula:

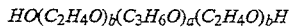

which may be employed in the preparation of the gels of the present invention are presented in Table I.

TABLE I

| Mol. Wt of hydrophobe* base (average) | Wt percent of hydrophile** (Average) | Approx. total mol. wt. of copolymer |
|---|---|---|
| 2250 | 50 | 4600 |
| 2250 | 70 | 7500 |
| 2250 | 80 | 10750 |
| 2750 | 45 | 4910 |
| 2750 | 60 | 6450 |
| 2750 | 80 | 13500 |
| 3250 | 35 | 4910 |
| 3250 | 45 | 6050 |
| 3250 | 50 | 6550 |
| 3250 | 80 | 15500 |
| 4000 | 15 | 4710 |
| 4000 | 25 | 5340 |
| 4000 | 35 | 6150 |
| 4000 | 70 | 13500 |
| 4000 | 80 | 20000 |

*Hydrophobe base is the $(C_3H_6O)_a$ portion of the copolymer molecule.
**Hydrophile base is the $(C_2H_4O)_b$ portion of the copolymer molecule.

It should be noted that the molecular weight values used in this application are average molecular weights and will vary depending upon the method used to measure the molecular weights. It should be understood that the present invention is not limited by these molecular weights.

Not all of the block copolymers of the formula:

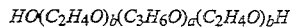

may be employed in the present invention. Because of the nature of aqueous solutions of these block copolymers, three variables affect the formation of the gels. These variables do not apply to the chemically branched or cross-linked copolymers. Therefore, it is necessary to recognize certain minima for the three variables. These variables are:

(1) the weight percent concentration of block copolymers in the gel;
(2) the molecular weight of the hydrophobe portion $(C_3H_6O)_a$; and
(3) the weight percent of the hydrophile portion $(C_2H_4O)_b$ of the copolymer.

These minimal define a minimum weight percent concentration of the block copolymer with a specific hydrophobe having a minimum weight percent of ethylene oxide that is necessary to form a gel. Thus, at the minimum concentration with a specific molecular weight hydrophobe, a minimum weight percent of ethylene oxide is required before a specific block copolymer will form a gel in an aqueous solution. Examples of minimum weight percent concentrations with specific molecular weight hydrophobes are set out in Table II.

TABLE II

| Mol. wt of hydrophobe base | Min. wt percent concentration to form a gel | Min. weight percent ethylene oxide required | Total mol. wt of block copolymer |
|---|---|---|---|
| 2250 | 40 | 50 | 4600 |
| 2750 | 40 | 45 | 4910 |
| 2750 | 30 | 60 | 6450 |
| 3250 | 30 | 35 | 4910 |
| 4000 | 50 | 15 | 4710 |
| 4000 | 30 | 35 | 6150 |
| 4000 | 20 | 70 | 13500 |

At least a 40 percent weight concentration of the block copolymer having a hydrophobe of at least 2250 molecular weight with at least about 50 weight percent of ethylene oxide condensed therewith will be necessary to form a gel in an aqueous solution. In all cases, the block copolymers above the minima indicated in Table I will form gels in aqueous solutions up to 90 weight percent concentration and higher. Above 90 weight percent concentration, however, the gels tend to become indistinguishable from the starting block copolymer itself. It is to be understood that the molecular weight of the hydrophobe may be other than those illustrated in Table I. Thus, for example, if a hydrophobe of about 2500 molecular weight is used, it is recognized that a gel may be formed from the block copolymer at a concentration of 40 weight percent in an aqueous solution where about 45 weight percent of ethylene oxide is present in the block copolymer.

From the information presented in Tables I and II, it can be seen that the following provisions must be maintained to prepare gel compositions in accordance with the present invention:

1. When "a" in the following formula

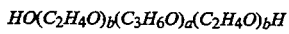

is an integer such that the average molecular weight of the hydrophobe is about 2250 Daltons, then the ethylene oxide content is from 50 to 90 weight percent of the copolymer, the total average molecular weight of the copolymer is from 4600 Daltons to 10,750 Daltons and the gel composition comprises from 40 to 50 weight percent of the copolymer.

2. When "a" in the following formula

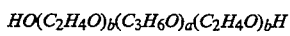

is an integer such that the average molecular weight of the hydrophobe is about 2750 Daltons, then the ethylene oxide content is from 45 to 90 weight percent of the copolymer, the total average molecular weight of the copolymer is from 4910 Daltons to 13,500 Daltons and the gel composition comprises from 40 to 50 weight percent of the copolymer.

3. When "a" in the following formula:

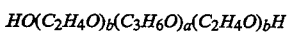

is an integer such that the average molecular weight of the hydrophobe is about 3250 Daltons, then the ethylene oxide content is from 35 to 90 weight percent of the copolymer, the total average molecular weight of the copolymer is from 4910 Daltons to 15,510 Daltons, and the gel composition comprises from 30 to 50 weight percent of the copolymer;

4. When "a" in the following formula:

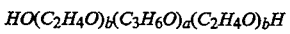

is an integer such that the average molecular weight of the hydrophobe is about 4000 Daltons, then the ethylene oxide content is from 35 to 90 weight percent of the copolymer, the total average molecular weight of the copolymer is from 6150 Daltons to 20,000 Daltons and the gel composition comprises from 30 to 50 weight percent of the copolymer, with the further proviso that when "a" in the formula is an integer such that the average molecular weight of the hydrophobe is about 4000 Daltons, the ethylene oxide content is from 70 to 90 weight percent, the total average molecular weight of the block polymer is from 16,000 Daltons to 20,000 Daltons and the gel composition comprises from 15 to 50 weight percent of the copolymer.

The preferred polyoxyethylene/polyoxypropylene copolymers are poloxamer 407 and poloxamer 338 (Pluronic® F127 and F108 available from the BASF Corporation, Parsippany, N.J.) The chemical formula of poloxamer 407 is α-hydro-omega-hydroxy-poly(oxyethylene)101-poly(oxypropylene)56-poly(oxyethylene)101.

The poloxamer 407 can also be represented by the following formula:

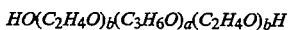

wherein the molecular weight of the hydrophobe $(C_3H_6O)$ is approximately 4000 Daltons and the total molecular weight of the compound is approximately 13,500 Daltons.

The poloxamer 338 can be represented by the following formula:

wherein the molecular weight of the hydrophobe $(C_3H_6O)_a$ is approximately 3250 Daltons and the molecule is made up of approximately 80% polyoxyethylene $(C_2H_4O)_b$.

The copolymer is preferably dissolved in an aqueous solution such as saline at a concentration of between 100 mg/ml and 500 mg/ml. The ideal concentration of copolymer in the aqueous solution will be different depending on the structure and size of the copolymer. The ideal concentration will also be dependent upon the required physical properties of the gel for that particular prosthesis. In general, the higher the concentration of the copolymer in the solution, the more rigid the gel will be.

Although the chemistry and the biocompatibility of the poloxamer gels of the present composition are well understood, little is known about the mechanical properties of these gels. The poloxamer gels fall within a category of materials called viscoelastic materials. Viscoelastic materials exhibit a combination of elastic (solid-like) and viscous (fluid-like) behavior.

The mechanical properties of the poloxamer gels can be altered by changing the concentration of block copolymer in solution, by changing the temperature of the solution, and, to a lesser extent, by varying the salt concentration of the solution. The proportions in a mixture of copolymers can be adjusted to obtain a specific viscosity. A salt can be added to the preparations to adjust the osmolality as needed.

Viscoelastic materials can be represented in simplest form by one of two models: The Maxwell model and the Kelvin Model.

In each case, the spring represents the elastic properties of the material while the dashpot represents the viscous properties. Characterization of a particular material involves determining the elastic and viscous constants, also called storage and loss moduli. In reality most viscoelastic materials exhibit more complex behavior than either of these models can account for. Typical materials of this type are better represented by a four element model combining properties of each of the simpler two element models represented above. These results in four constants which are very difficult to characterize experimentally.

Various methods of testing the viscoelasticity of gels are available. The creep test is a technically simple test to perform and gives direct values for computation of viscoelastic constant. In a creep test a sample is placed in a well and a force is applied. The force required to deform the sample is measured, as is the decrease in force as the sample changes shape in response to the force applied.

Capillary rheometers are used to measure the properties of polymer melts at various temperatures. While they provide a method of precise temperature control, the data generated consists of shear stress, shear rate, and viscosity. Viscosity is only indirectly related to the mechanical properties which will determine the suitability of the gel materials for the envisioned application.

Another method to determine the storage and loss moduli of materials is through vibration. A Bruel and Kjaer system, for example, applies a vibration to a beam shaped sample while monitoring the vibration output at the other end of the beam. By looking at the magnitude and phase change of the output signal versus the input signal, one can determine storage and loss moduli. However, this system is limited to solid samples, and the gel materials would not lend themselves to testing in this manner.

The mechanism of gel formation in ethyleneoxide-propyleneoxide block copolymer solution in water is thought to be through the dissociation of solvent molecules from the polymer chain and the onset of hydrogen bonding between polymer chains (primarily ethyleneoxide part) when the temperature of the polymer solution is raised. The gelation can also be achieved by chemically altering the structure of the copolymer. In this approach, a certain number of crosslinking sites are introduced to produce branched or crosslinked macromolecular network structure, without significantly altering the chemical composition. Gelation achieved by such procedure is less susceptible to temperature variations. The extent of gelation (and thus the rheological characteristics of the gel) can be controlled by changing the amount of crosslinking agents used.

Trifunctional monomers (such as 1-hydroxy 2,3-propyleneoxide in the case of propyleneoxide base) can be used as branching agents. An example of this type of branching is obtained by mixing propyleneoxide with a small amount of 1-hydroxy 2,3 propyleneoxide during the synthesis of the hydrophobe (propyleneoxide) chain. Controlled branching occurs during the hydrophobe formation as well as during subsequent hydrophilic chain formation. Chemical crosslinking can be obtained by using vinyl substituted crosslinking agents (such is vinyl oxirane for crosslinking a hydrophobe base), and crosslinking after the copolymer is formed. Chemical crosslinking can be also be achieved by numerous other routes. The advantage of chemical branching/crosslinking is that the polymer is less susceptible to chain fragmentation because covalent bonding is much stronger than hydrogen bonding.

The copolymers can be dissolved in an aqueous solution with a number of salts which can also be used to alter the viscosity of the gel. It has been found that although salt concentration can affect the viscoelastic properties of the gel composition, salt is not as effective as temperature or copolymer concentration. Sodium chloride can be used but is undesirable because of its lower radio translucency due to the higher atomic number of chlorine. Preferred salts include sodium lactate and sodium acetate. Although other cation salts such as those of calcium and potassium could be used, sodium salts are preferred because sodium is the most biocompatible cation. The radiolucency of the salt is related to the cube of the atomic number of the constituents, so those containing atoms with atomic numbers similar to natural tissue are much preferred.

The gel is normally made by dissolving the desired concentration of salt in deionized, sterilized water and adding the polyoxyethylene/polyoxypropylene block copolymer to create the desired osmolarity and viscosity.

It is to be understood that several different block copolymers can be used in combination to manufacture the gel. In addition, conventional gelling agents can be added to the copolymer solutions to provide additional gelling properties.

A salt is added to the copolymer gel solution to assure that the proper or desired osmotic properties or osmolarity is achieved and maintained for the system. For most applications, the gel is made osmotically equivalent to the normal osmolarity of the body (250-350 milliosmoles). Deviation from this, however, may be desirable for certain specialized applications. With respect to the selection of the salt material, two important considerations should be weighed. One is the relative radiolucency or permeability of the material to X-rays. The other is the ability of the body to eliminate the material should leakage occur. With respect to the radiolucency, in order to evaluate the female breast for development of small tumors, current practice is to regularly obtain X-ray mammograms. This is done by flattening the breast onto a horizontal radiographic plate and exposing it to an X-ray source for a standard exposure. It is well-known in the art to use 4 cm thick acrylic blocks as a breast tissue equivalent material to determine X-ray penetrance and optical density on the resultant processed X-ray film.

Mammary implants with silicone gels are not penetrated well by X-rays because of silicone's high atomic number. This is detrimental when evaluating a breast for tumors with mammography, as the silicone renders the processed X-ray film contrast unacceptable for evaluating underlying breast tissue. Saline filled prosthetics are an improvement over silicone gel filled prosthetics, but they also cause overexposure of surrounding breast tissue on processed X-ray film, obscuring the breast tissues. Normal saline filled implants at standard mammographic X-ray ensures result in X-ray film with an optical density of less than 1.2, and an X-ray penetrance of 9.2 milliroentgens. If one developed a gel filler that had a lower X-ray density than that of normal tissue, this would result in underexposure of the X-ray film and great loss of tissue detail surrounding the implant. Thus, a material having an X-ray density close to that of normal tissue is most desirable.

One of the advantages of the present invention is that it is generally more radiolucent than previous gels or normal saline. The bio-osmotic gel of the invention is designed to have an X-ray density close to that of natural breast tissue, thus allowing improved tissue discrimination and improved detection of very small tumors.

It is a generally established principle that the radiodensity of a pure material is directly proportional to the atomic number of that material cubed (Z3). For multiple species molecules, the atomic number of each element contributes a proportionate amount. Thus, salts using lower atomic number elements as constituents are generally preferred over those with elements having higher atomic numbers. For example, a saline filled implant would be an implant including a salt (NaCl) having equal numbers of sodium and chlorine atoms with atomic numbers of 11 and 17 respectively. The relatively high atomic number of chlorine renders the implant less radiolucent than is desired. Although in the combination of the present invention, saline has been found to exhibit better translucence than in previous combinations. The preferred implant gels in accordance with the present invention use a combination of polymer and sodium acetate, or sodium lactate. Sodium acetate has the lowest total "Z" value of the three.

Another consideration with respect to selection of the salt involves the ease of assimilation of the material into the body and ease of elimination, should leakage or rupture occur. For example, solutions containing large amounts of calcium or potassium salts could be used, but they would be more likely to cause disruption of ionic equilibrium in excitable tissues such as nerves and muscles, resulting in potential toxicity to these tissues. Sodium has been chosen as the preferred cation because it is the most extracellularly abundant bodily cation. It is otherwise quite acceptable for the gel and it is less radiopaque than other usable alkali or alkaline earth cations.

One of the major toxicities of the silicone gel prosthetics is their inability to be eliminated both from the local environment or from the body as a whole following rupture or leaking of the elastomeric container. The local deposition of silicone material is associated with toxicities ranging from the formation of a fibrous capsule to the development of autoimmune disease. Prosthetics containing a copolymer gel filled lumen will be free of these toxicities since any gel escaping the elastomeric container will be rapidly eliminated both from the local environment and from the body as a whole.

The elimination of block copolymers following parenteral or oral administration is well documented. Following intravenous injection, poloxamer 188 (Pluronic F68) rapidly distributes within the vascular and reticuloendothelial compartments over approximately 30 minutes. Elimination of the copolymer occurs via the kidneys and begins almost immediately following administration. The elimination half-life is between 1 and 3 hours, thus between 5 and 15 hours following intravenous administration more than 95% of the dose administered is eliminated from the body. The elimination of poloxamer 407 (Pluronic F127) has also been studied. Due to its higher molecular weight, the elimination half-life of poloxamer 407 (Pluronic F 127) is longer compared to poloxamer 188. Following intravenous administration, 33% of the administered material is recovered in a 6 hour period, with 68 to 75% of the administered dose recovered after 30 hours. Neither poloxamer 188 nor 407 are metabolized and both can be recovered in the urine unchanged. (See Pluronic Polyols, Toxicity & Irritation Data, BASF Corp., Industrial Chemicals Group, Wyandotte, Mich. 48192.)

Following oral administration both poloxamer 407 and 188 are quantitatively recovered from the feces illustrating that the copolymers are not absorbed into the body or metabolized.

It would be expected that following intramuscular or intraperitoneal administration (which may more closely mimic leakage from a prosthetic implant) clearance from the body may be slightly longer. However, the mechanisms for elimination (reticuloendothelial system and kidneys) would remain the same and thus one can confidently predict that poloxamer gels used to fill the lumen of prosthetic devices would be rapidly eliminated from the body if either rupture or leakage of the elastomeric container occurred.

Other pharmaceutically acceptable compositions can be added to the aqueous copolymer composition. For example, surfactants or lubricants can be added to the solution of copolymers to further reduce the possibility of a fold flaw rupture in the implant which could cause the implant to burst. Dermatan sulfate and other mucopolysaccharides are acceptable lubricants. Those which are naturally occurring and substantially free from anticoagulant activity are especially desirable, i.e. dermatan, chondroitan, hyaluronic acid. Another suitable lubricant is poloxamer 188 (Pluronic ® F68, BASF Corporation, Parsippany N.J.). The desired concentration of the lubricants in the present invention is up to 5% by weight. The preferred concentration is approximately 1% by weight In addition, conventional gelling composition can be added to the copolymer solution depending on the physical properties that are required for the particular prosthesis that is to be filled. Several different polyoxyethylene-polyoxypropylene block copolymers can be mixed to form the gel. Finally, the copolymers can be chemically branched or crosslinked to provide the desired gel consistency.

Dermatan or other non-anticoagulant glycosaminoglycans can be covalently linked to the external membrane. The glycosaminoglycans will resist the deposition of fibrin and thereby the formation of a fibrous capsule. Thus, the glycosaminoglycans will inhibit or prevent contracture.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

To prepare 100 g of block copolymer gel, 20 g of poloxamer 407 are weighed into a container which can be sealed and autoclaved. 80 g of deionized water are added to the container. The container is capped and mixed on a rotary shaker at 3° to 7° C. until the copolymer is completely dissolved. The solution will be clear when all of the copolymer is dissolved. The solution is then warmed to 37° C. and the viscosity is determined. If desired, the viscosity can be increased with the addition of a measured amount of poloxamer 407. To add poloxamer to the solution, the solution should be cooled to between approximately 3° to 7° C. The additional poloxamer is added and dissolved as described above. The solution is then warmed to 37° C. to determine the final viscosity. The container is then sealed and sterilized by autoclaving at 121° C. for 15 minutes and the sterilized solution is cooled to between approximately 3° to 7° C. and mixed thoroughly.

The solution is then transferred aseptically to an elastomeric lumen in the prosthesis. This transfer is preferably done at reduced temperature where the formulation is in the liquid state. The prosthesis is now ready for implantation.

EXAMPLE II

To prepare 100 g of block copolymer gel with dermatan sulfate as a lubricant, 19 g of poloxamer 407 are weighed into a container which can be sealed and autoclaved. 79 g of deionized water are added to the container. The container is capped and mixed on a rotary shaker at 3° to 7° C. until the copolymer is completely dissolved. The solution will be clear when all of the copolymer is dissolved. Add 1.00 g of dermatan sulfate (Scientific Protein Labs, Waunakee, Wis.). The container is sealed and mixed on a rotary shaker at 3° to 7° C. until the dermatan sulfate is completely in solution. The solution is then warmed to 37° C. to determine the final viscosity. Viscosity can be reduced by the addition deionized water and mixing at reduced temperature (3° to 7° C.). The container is then sealed and sterilized by autoclaving at 121° C. for 15 minutes after sterilization, the solution is cooled to between approximately 3° to 7° C. and mixed thoroughly.

The solution is then transferred aseptically to an elastomeric lumen in the prosthesis. This transfer is preferably done at reduced temperature where the formulation is in the liquid state. The prosthesis is now ready for implantation.

EXAMPLE III

To prepare 100 g of block copolymer gel with two copolymers, 10 g of poloxamer 407 and 12 g of poloxamer 338 are weighed into a container which can be sealed and autoclaved. 78 g of deionized water are added to the container. The container is capped and mixed on a rotary shaker at 3° to 7° C. until the copolymer is completely dissolved. The solution will be clear when all of the copolymer is dissolved. The solution is then warmed to 37° C. to determine the final viscosity. Viscosity can be reduced by the addition deionized water and mixing at reduced temperature (3° to 7° C.). The container is then sealed and sterilized by autoclaving at 121° C. for 15 minutes and the sterilized solution is cooled to between approximately 3° to 7° C. and mixed thoroughly.

The solution is then transferred aseptically to an elastomeric lumen in the prosthesis. This transfer is preferably done at reduced temperature where the formulation is in the liquid state. The prosthesis is now ready for implantation.

EXAMPLE IV

To a heated pressure reactor fitted with provisions to add reactants at elevated pressure, add 7.6 grams of propanediol and 11.2 grams of pure potassium hydroxide and heat the reactor to about 120° C. Slowly add a mixture of 295 grams of propyleneoxide and 3.9 grams of bioxirane (CAS Registry No. 1464-53-5) while maintaining the reactor pressure below 40 psi. At the end of the addition of propyleneoxide, slowly added 198 grams of ethyleneoxide gas while maintaining the reactor pressure below 40 psi. When all the ethyleneoxide is reacted, as indicated by the decreased pressure in the reactor, the reactor is cooled to room temperature and the polymer obtained is removed. This product is extracted with water to remove the catalyst. Upon soaking this polymer with water it forms a gel. The consistency of the gel depends upon the amount of water used.

EXAMPLE V

The following example illustrates the viscoelastic properties of the gels.

A relaxation test was used to measure the viscoelastic properties of the polyoxyethylene-polyoxypropylene gels and to provide a means for comparison of various gel formulations under different environmental test conditions. During a relaxation test, a known and fixed deformation is applied to a sample and the force required to maintain the deformation is monitored over a specific period of time. Upon initial deformation of the sample, the force required to maintain the deformation is high. As the viscous properties of the gels cause the gels to flow, the force declines over time, generally in an inverse exponential manner.

A test device was custom designed to hold a fixed amount of the gel. The test device consisted of a sample holder having a fixed base and a well contained therein into which the sample was deposited. The test device further compressed a plunger extending from a crosshead. The plunger fit into the well. The sample was deformed using the cylindrical plunger attached to the moving mechanically controlled crosshead. A load cell contained within the crosshead measured the force applied with the plunger.

The sample formulations tested are shown in Table III. Eighteen gel samples were tested. The samples included two different polymers, each at three different concentrations. In addition, at each polymer concentration, percent salt was varied from 0% to 1%. Each sample was to tested at room temperature and body temperature (37° Celsius). Test temperatures for each sample are shown in Table IV.

Samples were loaded in to the sample holder while in their liquid form. If the samples were not liquid at laboratory temperature, the samples were cooled in a refrigerator until they became liquid. A syringe was used to place 30 ml of sample into the sample holder, and the sample and sample holder were allowed to come to test temperature. The sample was then placed in the test machine and the testing was begun immediately. Preliminary measurements were taken to define the parameters for the test. Original deformation for all samples was 36% of the original height of the sample in the test well. The force was monitored for up to ten minutes, although in most samples, gel flow had reduced the force to very low levels compared with the initial values obtained.

"Room temperature" tests were conducted over a range from 24° to 28° C. During the test procedures, it was found that some of the gels remained liquid at laboratory temperature which varied between 22 and 25° C. In those cases, the formulations were heated slowly in a small oven until gelling was definite. Thus, each gel was tested at close as practical to a temperature just above its transition temperature. One would expect this to provide slightly different results than if each gel was tested at a fixed temperature such as 28° C.

For the tests conducted at 37° Celsius, samples were loaded into the sample holder, placed in an oven, and allowed to equilibrate at 37° C. The test fixture was then removed, placed into the test machine, and the test begun immediately. To control the temperature, the test fixture was built oversized so as to have significant thermal mass. Temperature measurements taken following the ten minute test found the samples to generally have cooled no more than two degrees. When combined with the fact that the most significant data is acquired during the first minute of testing, this is an acceptable means to control temperature.

All samples were tested successfully although some variation in "room temperature" was required. Test data is compiled in Table IV. Table IV includes the sample number (see Table III for corresponding formulation), test temperature, and the values for initial slope (a measure of the elastic stiffness), peak force (also a measure of elasticity), and the percent relaxation at four different time intervals (24 sec., 1, 3 and 10 minutes). The percent relaxation is defined as:

$$\% \text{ relaxation at time } t = \frac{\text{peak force minus force at time } t}{\text{peak force}} \times 100$$

The values give a measure of the time constant of the relaxation or viscous nature of the gel.

As an example of a typical reaction to the test, FIG. 1 illustrates the response of the material under test. As the gel is deformed it exhibits an initial stiffness which is quasilinear which is represented by the initial portion of the force-time plot. Viscoelastic flow then beings to take place resulting in the decreasing slope until the full deformation is reached at which time the force reaches a maximum. Material relaxation or viscoelastic flow continues to take place resulting in a decrease of the measured force in an inverse exponential manner.

Figure 2:
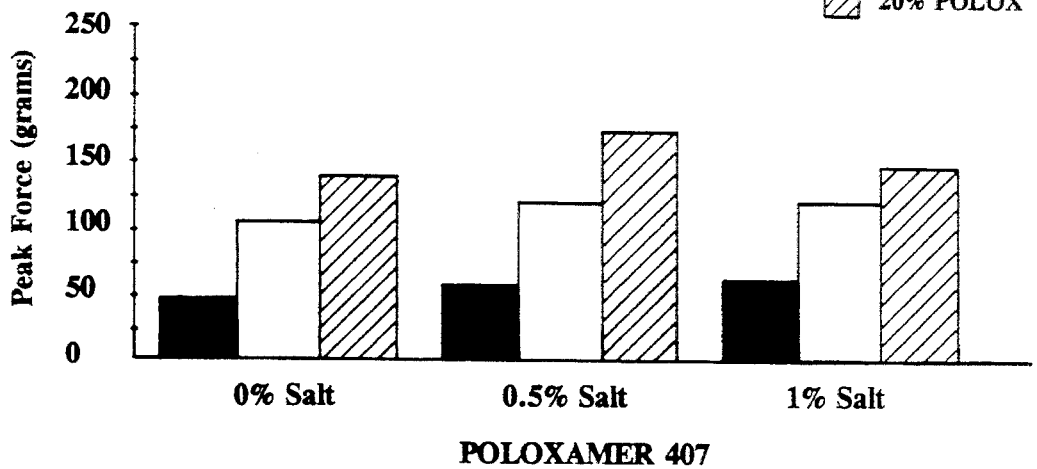
FIG. 2 shows the effect of polymer concentration on peak force at room temperature for poloxamer 407.
Figure 3:
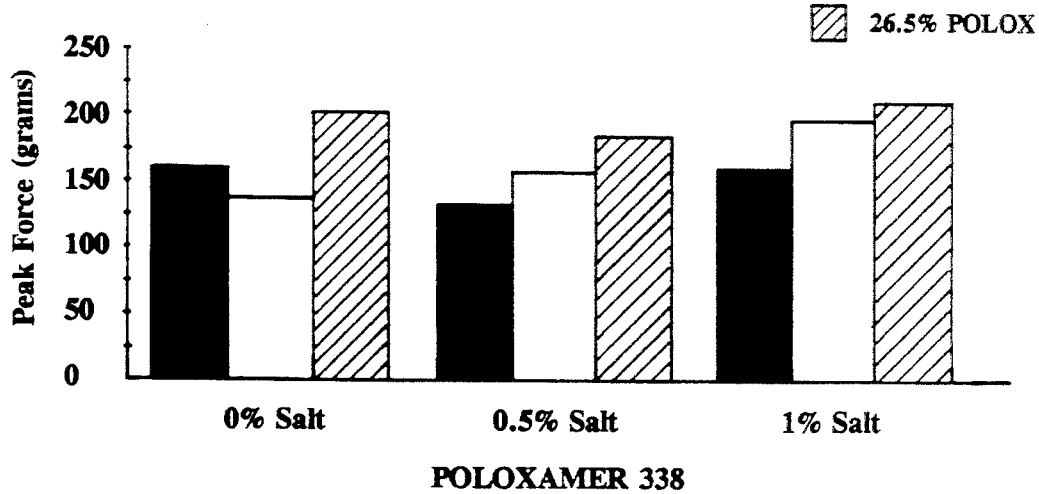
FIG. 3 shows the effect of polymer concentration on peak force at room temperature for poloxamer 338.
Figure 4:
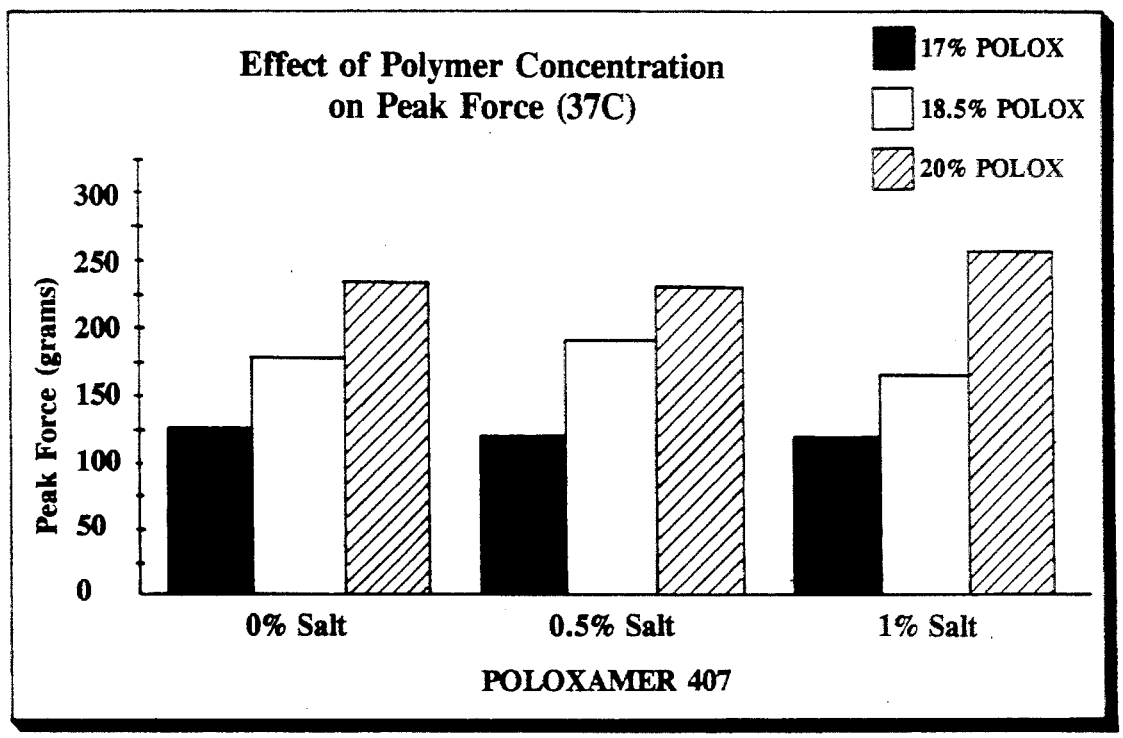
FIG. 4 shows the effect of polymer concentration on peak force at 37° C. for poloxamer 407.
Figure 5:
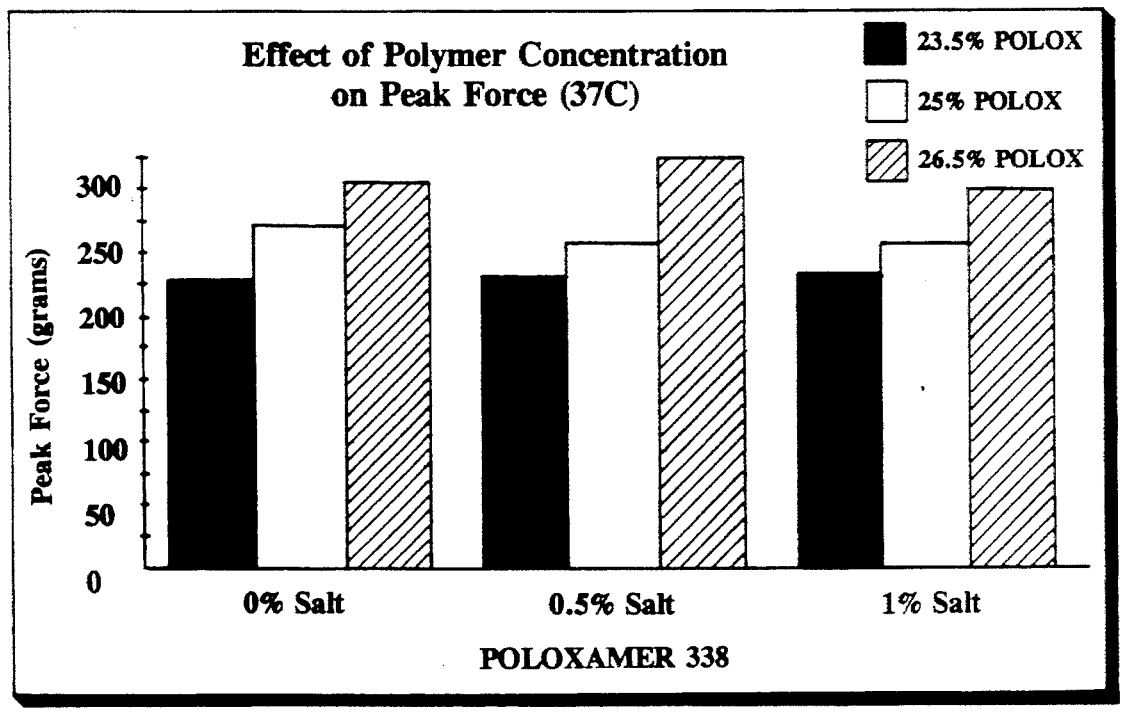
FIG. 5 shows the effect of polymer concentration on peak force at 37° C. for poloxamer 338.
Figure 6:
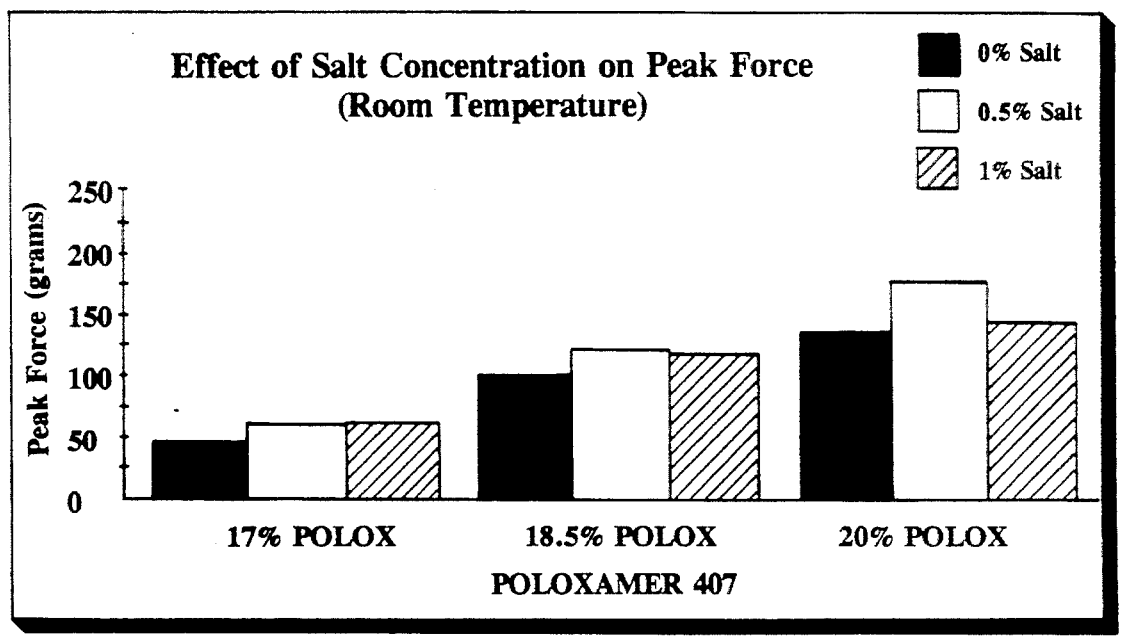
FIG. 6 shows the effect of salt concentration on peak force at room temperature for poloxamer 407.
Figure 7:
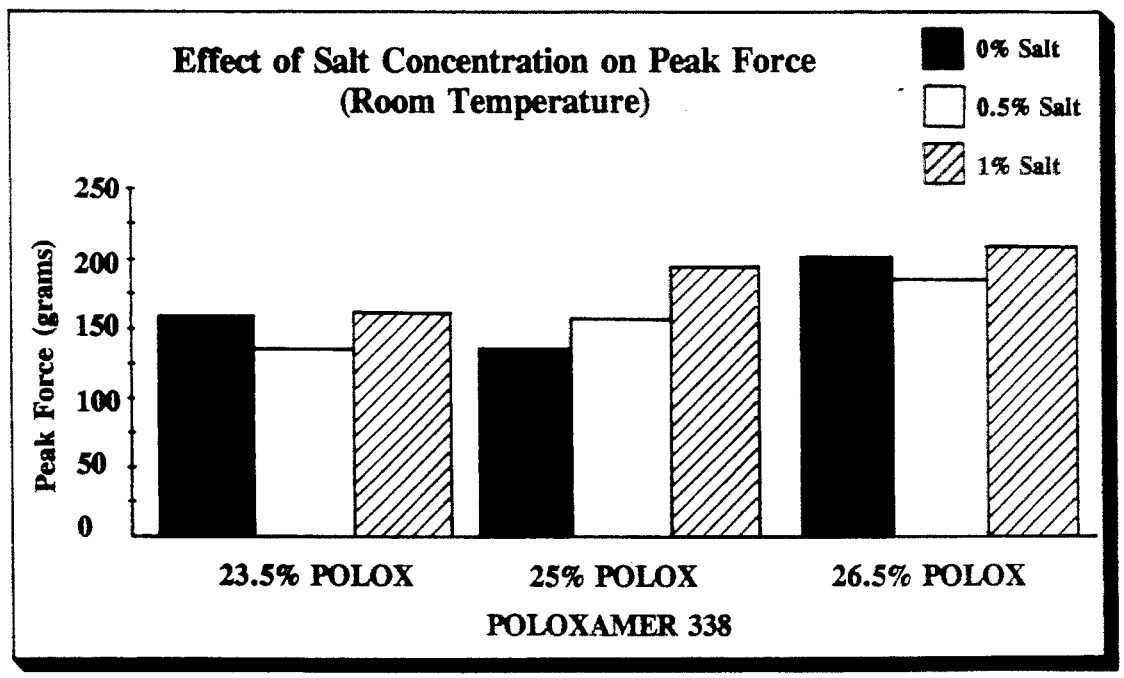
FIG. 7 shows the effect of salt concentration on peak force at room temperature for poloxamer 338.
Figure 8:
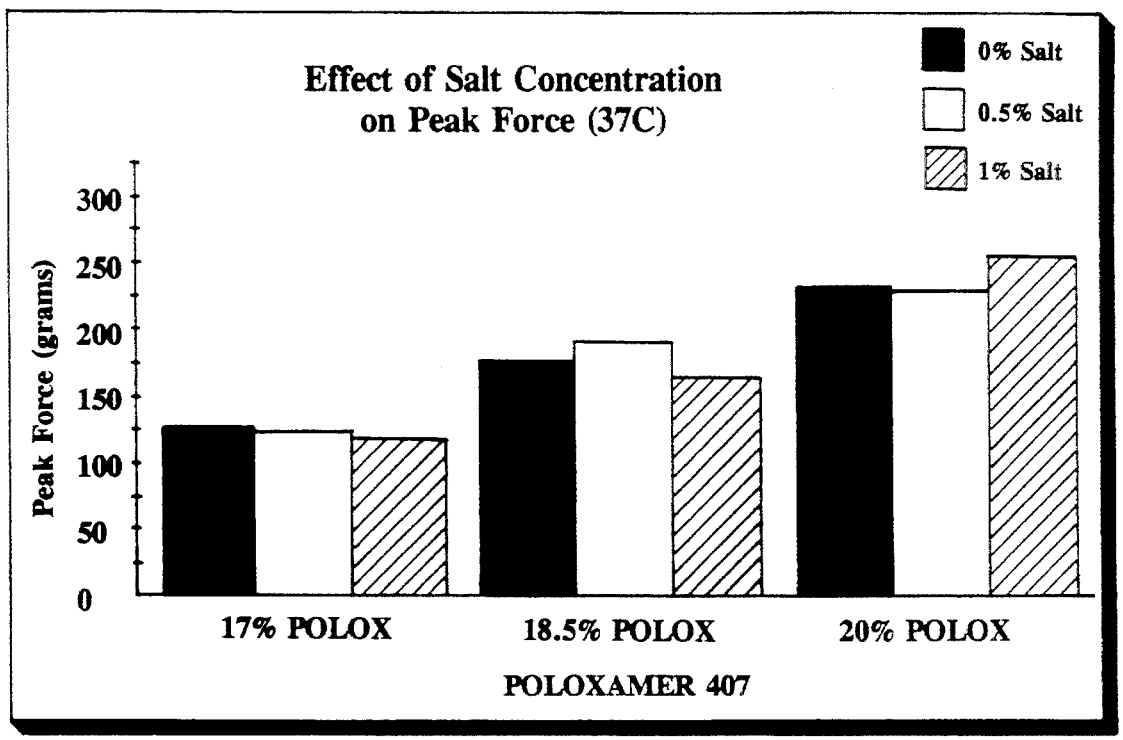
FIG. 8 shows the effect of salt concentration on peak force at 37° C. for poloxamer 407.
Figure 9:
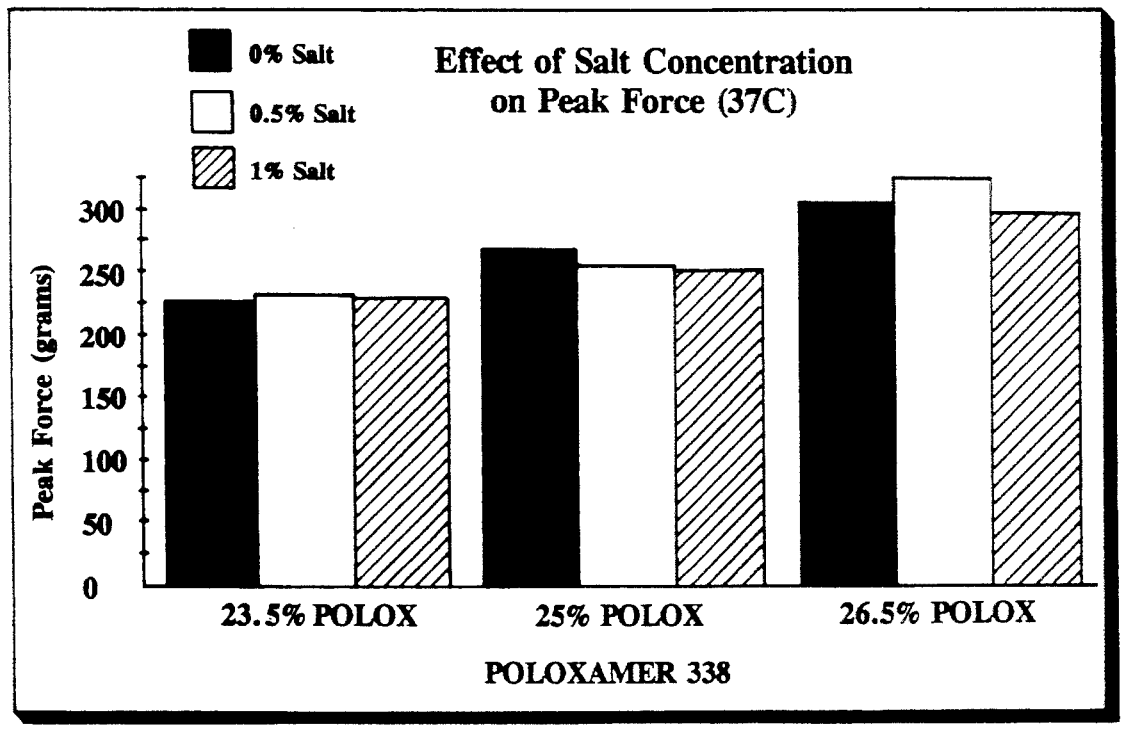
FIG. 9 shows the effect of salt concentration on peak force at 37° C. for poloxamer 338.

Both the peak force and the stiffness or slope describe the elastic stiffness of the gel. With the test procedure used, the peak force proved to be a more reliable measurement of viscoelasticity. FIGS. 2 and 3 illustrate the effects of polymer concentration on peak force at room temperature for poloxamer 407 and 338 respectively. Each figure clearly shows an increase in peak force with increasing concentration. The distinct separation in values indicates that this method could measure these effects in a statistically valid manner. Likewise, FIGS. 4 and 5 show the identical effect except at 37° C. While the absolute values are higher for Poloxamer 338 samples, the poloxamer 407 samples show a stronger effect of polymer concentration on peak force.

On the other hand, salt concentration, as illustrated in FIG. 6 through 9, has little, if any, effect on peak force. While not necessarily conclusive, it appears that salt concentration up to 1% has a limited effect on the elastic properties of the poloxamer gels.

Temperature effects are illustrated in FIGS. 10 and 11. Zero % salt and 1% salt samples are shown separately in these two figures. There is a clear and significant effect of test temperature on the gel mechanical properties, demonstrating increased stiffness at 37° C. This is confirmed by the plots of stiffness or initial slope as shown in FIG. 12.

Evaluation of the relaxation portion of the test curves is somewhat more complex. Analysis of the data showed no effect of salt concentration on the relaxation properties (as was also the case with the peak force and stiffness). Thus for clarity we have used the means of the relaxation values for all samples were used to show the effects of polymer composition on relaxation in FIGS. 13 and 14. In all cases the samples with lower polymer concentration showed a shorter time constant for relaxation. That is, they exhibited greater viscous flow to reduce the applied force. However, it is important to note that the relaxation values are comparable for many of the samples. Also, overall the poloxamer 338 samples exhibited greater relaxation than the poloxamer 407 samples. For example, averaging the percent relaxation value at 1 minute over all samples within a polymer type results in means of 78.1% relaxation for poloxamer 407 samples and 88.2% for poloxamer 338 samples.

Figure 15:
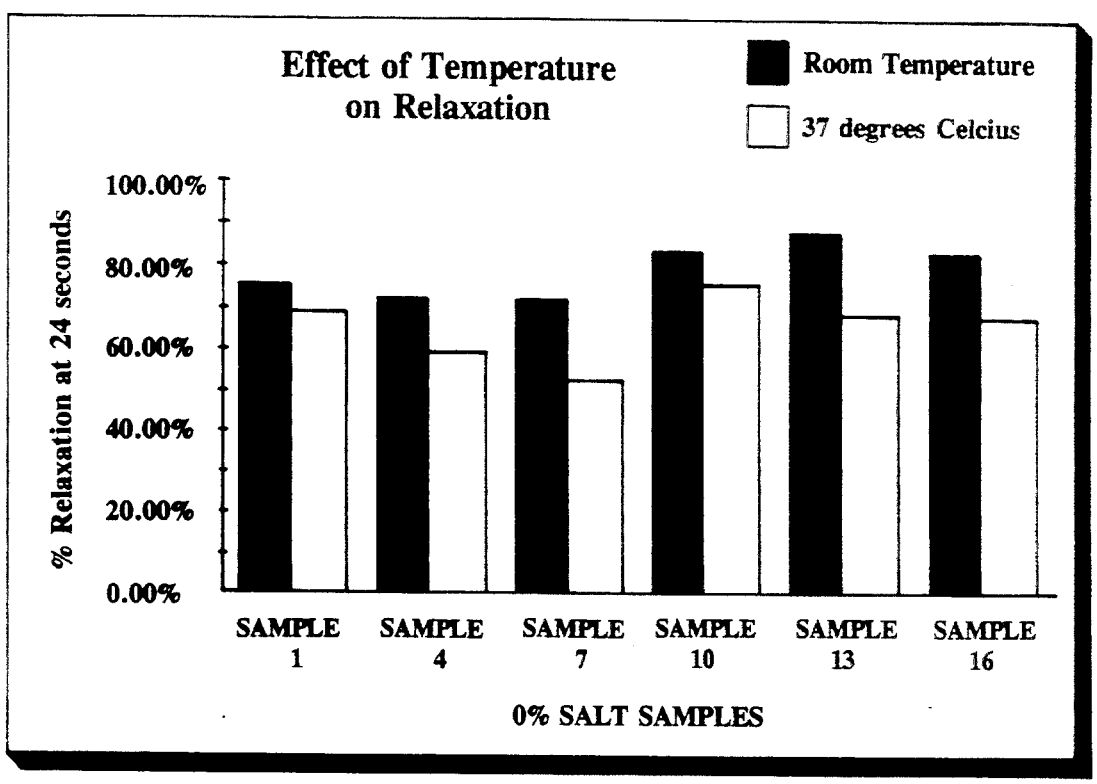
FIG. 15 shows percent relaxation at 24 seconds at room temperature and at 37° C. with 0% salt.
Figure 16:
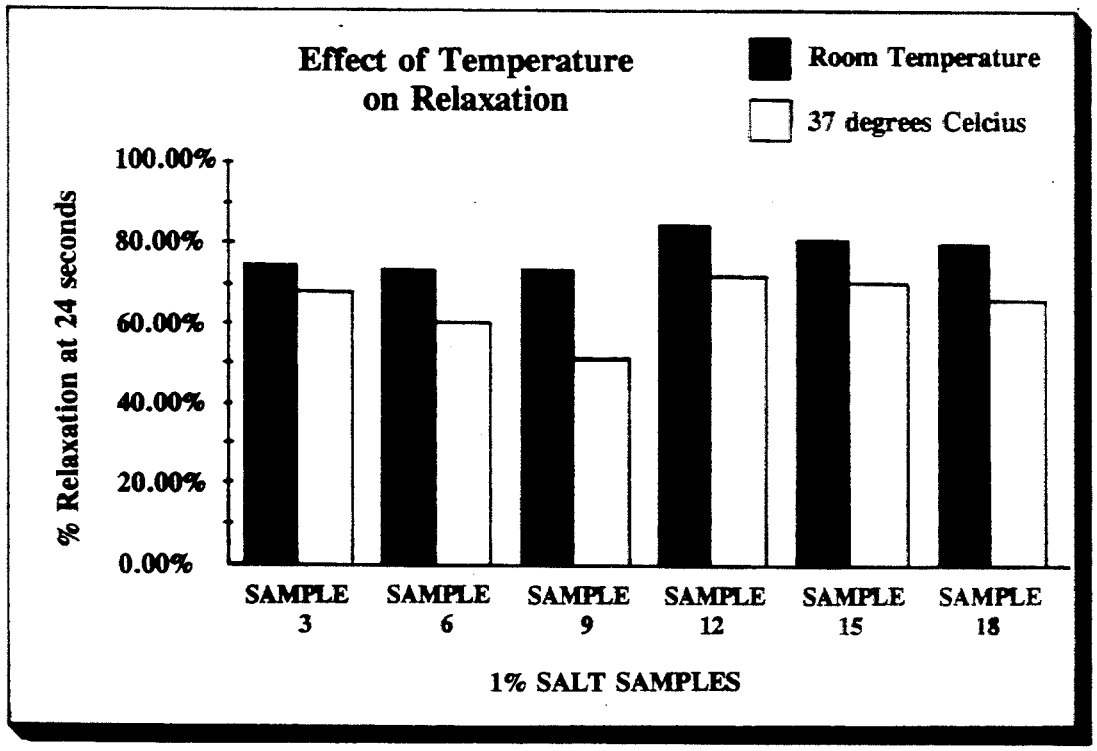
FIG. 16 shows percent relaxation at 24 seconds at room temperature and at 37° C. with 1% salt.
Figure 17:
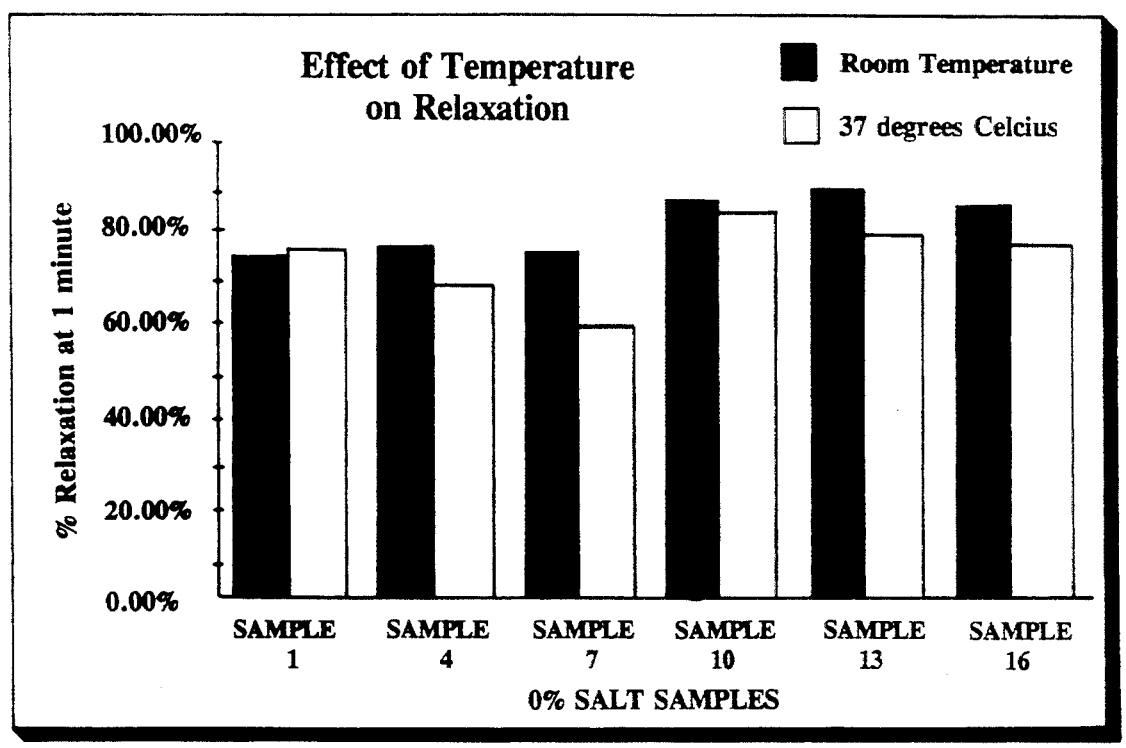
FIG. 17 shows percent relaxation at one minute at room temperature and at 37° C. with 0% salt.
Figure 18:
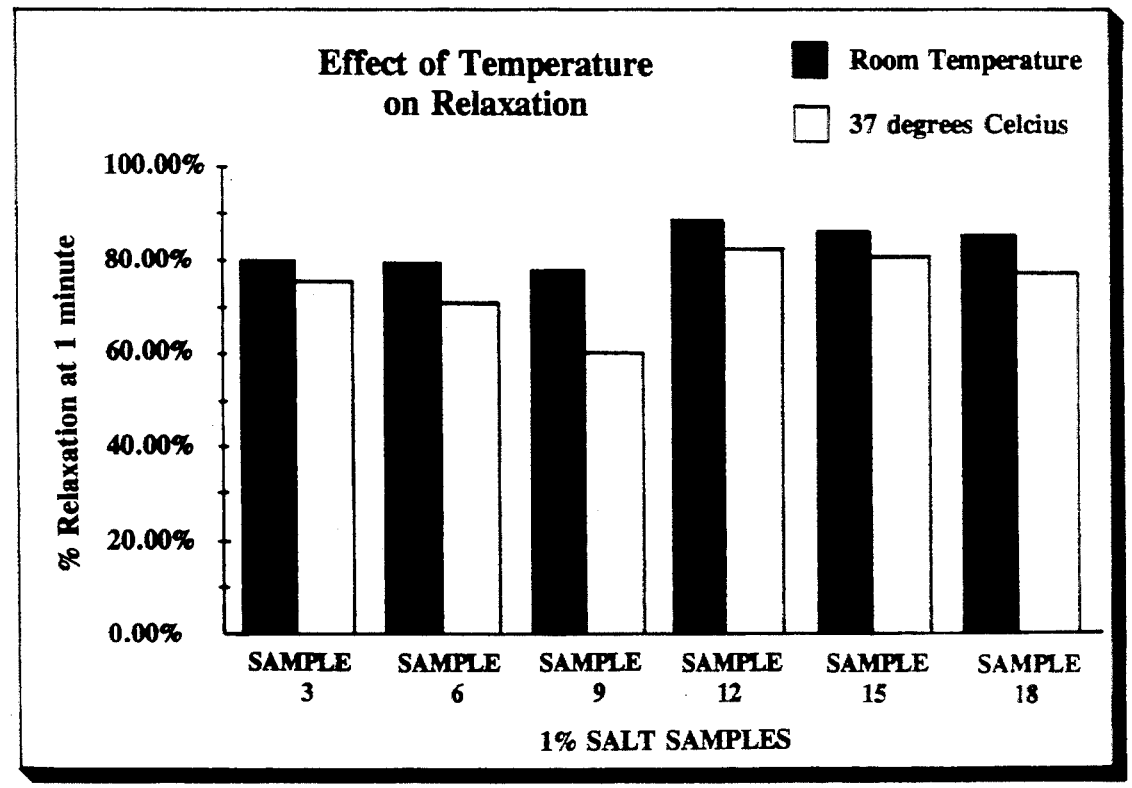
FIG. 18 shows percent relaxation at one minute at room temperature and at 37° C. with 1% salt.

As to effects of temperature, as would be expected the room temperature samples demonstrated faster relaxation than the body temperature samples of same composition. This difference exists at both 24 seconds (FIG. 15 and 16) and at 1 minute (FIG. 17 and 18), although at one minute the differences are decreased.

It should be understood, of course, that the foregoing relates only to a preferred embodiment of the present invention and that numerous modifications or alterations may be made therein without departing from the spirit and the scope of the invention as set forth in the appended claims.

TABLE III

| FORMULATION | POLOXAMER | % POLOX | % SALT | IN SOL'N | GEL AT 22–23° C. | GEL AT 25° C. | GEL AT 30° C. | GEL AT 37° C. |
|---|---|---|---|---|---|---|---|---|
| 1 | 407 | 17 | 0 | YES | NO | YES | YES | YES |
| 2 | 407 | 17 | 0.5 | YES | NO | YES | YES | YES |

TABLE III-continued

GEL FORMULATIONS

| FORMULA-TION | POLOX-AMER | % POLOX | % SALT | IN SOL'N | GEL AT 22-23° C. | GEL AT 25° C. | GEL AT 30° C. | GEL AT 37° C. |
|---|---|---|---|---|---|---|---|---|
| 3 | 407 | 17 | 1 | YES | NO | YES | YES | YES |
| 4 | 407 | 18.5 | 0 | YES | YES | YES | YES | YES |
| 5 | 407 | 18.5 | 0.5 | YES | YES | YES | YES | YES |
| 6 | 407 | 18.5 | 1 | YES | YES | YES | YES | YES |
| 7 | 407 | 20 | 0 | YES | YES | YES | YES | YES |
| 8 | 407 | 20 | 0.5 | YES | YES | YES | YES | YES |
| 9 | 407 | 20 | 1 | YES | YES | YES | YES | YES |
| 10 | 338 | 23.5 | 0 | YES | NO | YES | YES | YES |
| 11 | 338 | 23.5 | 0.5 | YES | YES | YES | YES | YES |
| 12 | 338 | 23.5 | 1 | YES | YES | YES | YES | YES |
| 13 | 338 | 25 | 0 | YES | YES | YES | YES | YES |
| 14 | 338 | 25 | 0.5 | YES | YES | YES | YES | YES |
| 15 | 338 | 25 | 1 | YES | YES | YES | YES | YES |
| 16 | 338 | 26.5 | 0 | YES | YES | YES | YES | YES |
| 17 | 338 | 26.5 | 0.5 | YES | YES | YES | YES | YES |
| 18 | 338 | 26.5 | 1 | YES | YES | YES | YES | YES |

TABLE IV

| Sample No. | Temp. (C) | Intial Slope (g/mm) | Peak Force (g) | % Relax at 24 sec. | % Relax at 1 min. | % Relax at 3 min. | % Relax at 10 min. |
|---|---|---|---|---|---|---|---|
| 1 | 28 | 15 | 47 | 75.53% | 75.96% | 75.96% | 76.60% |
| 2 | 28 | 35 | 59 | 76.27% | 80.00% | 81.36% | 81.69% |
| 3 | 28 | 40 | 63.8 | 74.92% | 79.94% | 83.86% | 84.64% |
| 4 | 27 | 35 | 104 | 72.12% | 77.88% | 83.17% | 89.62% |
| 5 | 26 | 45 | 122 | 73.77% | 78.69% | 82.95% | 87.46% |
| 6 | 27 | 34 | 120.8 | 73.68% | 79.72% | 85.10% | 88.41% |
| 7 | 26 | 27 | 140.5 | 72.24% | 77.22% | 81.49% | 86.12% |
| 8 | 26 | 49 | 177.5 | 68.85% | 74.37% | 78.87% | 83.77% |
| 9 | 24 | 40 | 148.7 | 74.45% | 78.82% | 82.52% | 87.22% |
| 10 | 28 | 65 | 159.3 | 83.99% | 88.20% | 90.90% | 91.96% |
| 11 | 26 | 73 | 134.5 | 85.65% | 88.48% | 89.74% | 91.82% |
| 12 | 26 | 50 | 161.8 | 85.48% | 88.88% | 91.35% | 92.58% |
| 13 | 26 | 75 | 137 | 87.96% | 90.36% | 90.88% | 91.02% |
| 14 | 26 | 30 | 157 | 85.03% | 88.98% | 91.72% | 93.12% |
| 15 | 26 | 45 | 196.5 | 81.68% | 86.51% | 90.08% | 92.88% |
| 16 | 26 | 50 | 202 | 83.17% | 87.13% | 90.10% | 93.32% |
| 17 | 24 | 75 | 185 | 85.95% | 89.19% | 91.46% | 92.97% |
| 18 | 24 | 70 | 210 | 80.24% | 85.77% | 88.86% | 91.82% |
| 1 | 37 | 50 | 127 | 68.50% | 76.38% | 84.25% | 92.91% |
| 2 | 37 | 42 | 122 | 68.85% | 78.69% | 87.70% | 95.90% |
| 3 | 37 | 38 | 120 | 67.50% | 75.00% | 84.17% | 96.67% |
| 4 | 37 | 71 | 179 | 59.22% | 69.27% | 78.77% | 92.18% |
| 5 | 37 | 94 | 192 | 59.38% | 67.19% | 76.56% | 86.46% |
| 6 | 37 | 50 | 165 | 60.61% | 71.52% | 87.88% | na |
| 7 | 37 | 63 | 236 | 52.75% | 60.59% | 74.58% | 97.03% |
| 8 | 37 | 81 | 232 | 52.59% | 61.64% | 75.43% | 95.69% |
| 9 | 37 | 75 | 258 | 51.55% | 60.85% | 71.32% | 85.66% |
| 10 | 37 | 64 | 227 | 75.77% | 85.46% | 96.70% | na |
| 11 | 37 | 84 | 231 | 74.03% | 84.85% | 98.27% | na |
| 12 | 37 | 100 | 231 | 72.73% | 82.68% | 93.51% | na |
| 13 | 37 | 88 | 270 | 68.52% | 80.37% | 94.44% | na |
| 14 | 37 | 75 | 256 | 69.53% | 81.25% | 90.23% | 97.27% |
| 15 | 37 | 66 | 254 | 70.47% | 80.71% | 90.55% | 98.82% |
| 16 | 37 | 98 | 305 | 67.21% | 77.70% | 88.52% | 99.34% |
| 17 | 37 | 83 | 324 | 66.05% | 75.93% | 87.04% | 99.38% |
| 18 | 37 | 133 | 298 | 66.11% | 77.52% | 90.27% | na |

We claim:

1. A method for providing a prosthesis approximating the consistency of human or animal tissue comprising the step of filling the lumen of the prosthesis with an aqueous solution of a polyoxyethylene-polyoxypropylene block copolymer having the following formula:

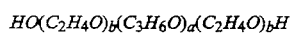

wherein a is an integer such that the hydrophobe represented by $(C_3H_6O)_a$ has a molecular weight of between 1750 and 6000 daltons and b is an integer such that the hydrophile portion represented by $(C_2H_4O)_b$ constitutes from about 50 to 90 percent by weight of the copolymer.

2. The method of claim 1, wherein the hydrophobe represented by $(C_3H_6O)_a$ has an average molecular weight of between approximately 1750 and 4000 Daltons.

3. The method of claim 1, wherein the hydrophobe represented by $(C_3H_6O)_a$ has an average molecular weight of approximately 4000 Daltons.

4. A soft tissue prosthesis [with]comprising a lumen and a filler, wherein the filler comprises an aqueous solution of a polyoxyethylene-polyoxypropylene block copolymer having the following formula:

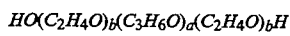

wherein a is an integer such that the hydrophobe represented by $(C_3H_6O)_a$ has a molecular weight of between 1750 and 6000 daltons and b is an integer such that the hydrophile portion represented by $(C_2H_4O)_b$ constitutes from about 50 to 90 percent by weight of the copolymer.

5. The prosthesis of claim 4, wherein the hydrophobe represented by $(C_3H_6O)_a$ has an average molecular weight of between approximately 2750 and 4000 Daltons.

6. The prosthesis of claim 4, wherein the hydrophobe represented by $(C_3H_6O)_a$ has an average molecular weight of approximately 4000 Daltons.

7. The prosthesis of claim 4, wherein the prosthesis is a breast implant.

8. A method of implanting a prosthesis into a human or animal comprising the steps of:
  implanting the lumen of the prosthesis into the body of the human or animal;
  filling the lumen with an aqueous solution of polyoxyethylene-polyoxypropylene block copolymer having the following formula:

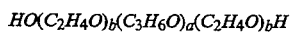

wherein a is an integer such that the hydrophobe represented by $(C_3H_6O)_a$ has a molecular weight of between 1750 and 6000 daltons and b is an integer such that the hydrophile portion represented by $(C_2H_4O)_b$ constitutes from about 50 to 90 percent by weight of the copolymer; and,
  allowing the solution to gel.

9. The method of claim 8, wherein the hydrophobe represented by $(C_3H_6O)_a$ has an average molecular weight of between approximately 2750 and 4000 Daltons.

10. The method of claim 8, wherein the hydrophobe represented by $(C_3H_6O)_a$ has an average molecular weight of approximately 4000 Daltons.

11. The method of claim 8, wherein the prosthesis is a breast implant.

12. The method of claim 8, wherein the gel further contains an effective amount of dermatan sulfate.

13. The method of claim 1, further comprising the step of adding a biologically compatible salt to the polyoxyethylene-polyoxypropylene block copolymer solution.

14. The method of claim 13 wherein the salt has a low radiodensity.

15. The soft tissue prosthesis of claim 4, wherein the filler further comprises a salt.

16. The soft tissue prosthesis of claim 4 wherein the filler is radiolucent.

* * * * *